United States Patent
Deng et al.

(10) Patent No.: US 11,446,410 B2
(45) Date of Patent: Sep. 20, 2022

(54) CHEMICALLY STRENGTHENED BIOACTIVE GLASS-CERAMICS

(71) Applicant: CORNING INCORPORATED, Corning, NY (US)

(72) Inventors: Huayun Deng, Painted Post, NY (US); Qiang Fu, Painted Post, NY (US); John Christopher Mauro, Boalsburg, PA (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 17/076,410

(22) Filed: Oct. 21, 2020

(65) Prior Publication Data
US 2021/0030920 A1    Feb. 4, 2021

Related U.S. Application Data (62) Division of application No. 16/202,786, filed on Nov. 28, 2018, now Pat. No. 10,857,259.

(60) Provisional application No. 62/591,438, filed on Nov. 28, 2017.

(51) Int. Cl.
| | | |
|---|---|---|
| C03C 10/04 | (2006.01) | |
| C03C 10/12 | (2006.01) | |
| A61L 27/10 | (2006.01) | |
| A61L 24/02 | (2006.01) | |
| C03C 21/00 | (2006.01) | |
| C03C 10/00 | (2006.01) | |
| C03C 10/16 | (2006.01) | |
| C03C 4/00 | (2006.01) | |
| C03C 4/18 | (2006.01) | |
| A61L 24/00 | (2006.01) | |
| A61L 27/12 | (2006.01) | |
| A61L 27/04 | (2006.01) | |
| A61L 27/02 | (2006.01) | |
| C03C 3/097 | (2006.01) | |
| C03C 3/118 | (2006.01) | |
| C03C 3/112 | (2006.01) | |
| C03B 25/02 | (2006.01) | |

(52) U.S. Cl.
CPC .......... A61L 27/105 (2013.01); A61L 24/001 (2013.01); A61L 24/02 (2013.01); A61L 27/025 (2013.01); A61L 27/047 (2013.01); A61L 27/12 (2013.01); C03C 3/097 (2013.01); C03C 3/112 (2013.01); C03C 3/118 (2013.01); C03C 4/0021 (2013.01); C03C 4/18 (2013.01); C03C 10/0027 (2013.01); C03C 10/0054 (2013.01); C03C 10/16 (2013.01); C03C 21/002 (2013.01); A61L 2430/02 (2013.01); C03B 25/02 (2013.01); C03C 2204/00 (2013.01)

(58) Field of Classification Search
CPC . C03C 10/00; C03C 10/0009; C03C 10/0027; A61L 27/105
See application file for complete search history.

(56) References Cited

U.S. PATENT DOCUMENTS

| | | | | |
|---|---|---|---|---|
| 2,532,386 | A ‡ | 12/1950 | Armistead | C03C 3/062 501/74 |
| 2,978,339 | A | 4/1961 | Franklin et al. | |
| 2,987,339 | A ‡ | 4/1961 | Kaplan | B66C 1/24 294/81 |
| 3,323,888 | A ‡ | 6/1967 | Searight | C03B 19/109 65/21 |
| 3,778,335 | A ‡ | 12/1973 | Boyd | C03C 21/00 428/33 |
| 3,790,430 | A ‡ | 2/1974 | Mochel | C03C 15/00 428/41 |
| 4,083,727 | A ‡ | 4/1978 | Andrus | C03C 10/0027 252/62 |
| 4,084,972 | A ‡ | 4/1978 | Andrus | C03C 10/0009 252/51 |
| 4,126,437 | A ‡ | 11/1978 | O'Horo | C03C 10/0081 252/62 |
| 4,140,645 | A ‡ | 2/1979 | Beall | H01F 1/37 252/62 |
| 4,233,169 | A ‡ | 11/1980 | Beall | C03C 3/089 252/62 |
| 4,323,056 | A ‡ | 4/1982 | Borrelli | A61K 9/5094 600/10 |
| 4,340,693 | A ‡ | 7/1982 | Drake | C03C 12/00 525/33 |
| 4,391,646 | A | 7/1983 | Howell | |
| 4,889,707 | A ‡ | 12/1989 | Day | A61K 9/1611 424/1 |
| 5,024,973 | A | 6/1991 | Kondo et al. | |
| 5,081,394 | A ‡ | 1/1992 | Morishita | H01J 29/327 313/46 |

(Continued)

FOREIGN PATENT DOCUMENTS

| | | | | |
|---|---|---|---|---|
| CA | 2577628 | C ‡ | 3/2006 | .......... A61K 8/8176 |
| CA | 2926665 | A1 ‡ | 5/2015 | |

(Continued)

OTHER PUBLICATIONS

Cao et al; "Bioactive Materials"; Ceramics International, 22, (1996) 493-507.‡
Cao et al; "Methods for Biomimetic Remineralization of Human Dentine: A Systematic Review"; Int. J. Mol. Sci. (2015) 16; pp. 4615-4627.‡
Bunker, et al., "Phosphate Glass Dissolution in Aqueous Solutions", Journal of Non-Crystalline Solids 64 (1984) 291-316.‡

(Continued)

*Primary Examiner* — Karl E Group (57) ABSTRACT

A chemically strengthened bioactive glass-ceramic composition as defined herein. Also disclosed are methods of making and using the disclosed compositions.

9 Claims, 4 Drawing Sheets

(56) References Cited

U.S. PATENT DOCUMENTS

| | | | |
|---|---|---|---|
| 5,153,070 A ‡ | 10/1992 | Andrus | C03C 8/02 428/36 |
| 5,217,928 A | 6/1993 | Goetz et al. | |
| 5,252,523 A | 10/1993 | Beall et al. | |
| 5,648,124 A ‡ | 7/1997 | Sutor | B01J 13/02 427/12 |
| 5,674,790 A ‡ | 10/1997 | Araujo | C03C 3/083 501/52 |
| 5,849,816 A ‡ | 12/1998 | Suskind | A61F 13/534 523/20 |
| 5,876,452 A ‡ | 3/1999 | Athanasiou | A61F 2/28 424/42 |
| 6,034,014 A ‡ | 3/2000 | Rapp | C03C 13/00 501/35 |
| 6,214,471 B1 ‡ | 4/2001 | Beall | C03C 3/145 428/34 |
| 6,254,981 B1 ‡ | 7/2001 | Castle | B01J 2/16 428/32 |
| 6,280,863 B1 ‡ | 8/2001 | Frank | A61K 6/824 428/70 |
| 6,328,990 B1 ‡ | 12/2001 | Ducheyne | A61L 27/32 424/42 |
| 6,338,751 B1 ‡ | 1/2002 | Litkowski | C03C 3/097 106/35 |
| 6,506,399 B2 ‡ | 1/2003 | Donovan | A61K 38/4893 424/42 |
| 6,514,892 B1 ‡ | 2/2003 | Kasai | C03C 12/02 428/32 |
| 6,802,894 B2 ‡ | 10/2004 | Brodkin | A61K 6/17 106/35 |
| 6,838,171 B2 ‡ | 1/2005 | Nomura | C03C 12/00 428/36 |
| 6,852,656 B1 ‡ | 2/2005 | La Greca | C03C 13/00 501/35 |
| 7,047,634 B2 | 5/2006 | Nakamura | |
| 7,047,637 B2 ‡ | 5/2006 | deRochemont | B32B 15/00 29/855 |
| 7,166,548 B2 ‡ | 1/2007 | Apel | A61K 6/824 501/5 |
| 7,166,549 B2 ‡ | 1/2007 | Fechner | A61Q 17/005 501/56 |
| 7,192,602 B2 ‡ | 3/2007 | Fechner | C03C 4/0007 424/40 |
| 7,316,740 B2 | 1/2008 | Schweiger et al. | |
| 7,597,900 B2 ‡ | 10/2009 | Zimmer | A61K 8/25 424/40 |
| 7,704,903 B2 ‡ | 4/2010 | Seneschal | A61Q 17/005 501/45 |
| 7,709,027 B2 ‡ | 5/2010 | Fechner | A61P 31/04 424/48 |
| 7,905,115 B2 ‡ | 3/2011 | Rake | A61L 27/10 65/466 |
| 7,989,065 B2 ‡ | 8/2011 | Winstead | G01N 33/5434 428/40 |
| 8,080,490 B2 ‡ | 12/2011 | Fechner | A61Q 17/005 501/24 |
| 8,173,154 B2 ‡ | 5/2012 | Jung | A61K 33/34 424/44 |
| 8,637,300 B2 ‡ | 1/2014 | Ruf | C12N 11/14 435/26 |
| 9,056,045 B2 ‡ | 6/2015 | Hughes | A61P 9/10 |
| 9,084,844 B2 ‡ | 7/2015 | Vallittu | A61F 2/08 |
| 9,101,439 B2 | 8/2015 | Ritzberger et al. | |
| 9,168,272 B2 ‡ | 10/2015 | Hill | C03C 4/0007 |
| 9,232,989 B2 | 1/2016 | Ritzberger et al. | |
| 9,238,044 B2 | 1/2016 | Da et al. | |
| 9,241,879 B2 ‡ | 1/2016 | Castillo | C03C 4/0021 |
| 9,326,995 B2 ‡ | 5/2016 | Stucky | A61K 33/00 |
| 9,498,459 B2 ‡ | 11/2016 | Pomrink | A61P 3/00 |
| 9,622,483 B2 ‡ | 4/2017 | Bookbinder | C03C 10/0009 |
| 9,688,567 B2 ‡ | 6/2017 | Rampf | C03C 1/00 |
| 9,701,573 B2 ‡ | 7/2017 | Beall | C03C 3/097 |
| 9,731,995 B2 * | 8/2017 | Kim | C04B 41/009 |
| 2004/0120908 A1 ‡ | 6/2004 | Cohen | A61K 8/0241 424/63 |
| 2004/0166172 A1 | 8/2004 | Rosati et al. | |
| 2004/0228905 A1 | 11/2004 | Greenspan et al. | |
| 2005/0118236 A1 | 6/2005 | Qiu et al. | |
| 2005/0142077 A1 ‡ | 6/2005 | Zimmer | C03C 4/0007 424/57 |
| 2005/0158395 A1 | 7/2005 | Zimmermann et al. | |
| 2005/0233888 A1 | 10/2005 | Seneschal et al. | |
| 2006/0127427 A1 | 6/2006 | Vernice et al. | |
| 2006/0292280 A1 ‡ | 12/2006 | Soper | A23L 27/72 426/53 |
| 2007/0122356 A1 ‡ | 5/2007 | Kessler | A61K 6/836 424/49 |
| 2007/0281033 A1 | 12/2007 | Rochat | |
| 2008/0214428 A1 ‡ | 9/2008 | Orlich | C11D 17/0039 510/40 |
| 2008/0233201 A1 | 9/2008 | Royere et al. | |
| 2009/0208428 A1 | 8/2009 | Hill et al. | |
| 2009/0258778 A1 | 10/2009 | Castillo | |
| 2009/0324668 A1 | 12/2009 | Kangasniemi et al. | |
| 2011/0008293 A1 ‡ | 1/2011 | Bhandari | A23L 27/72 424/93 |
| 2011/0009254 A1 | 1/2011 | Schweiger et al. | |
| 2011/0152057 A1 | 6/2011 | Qi | |
| 2012/0020898 A1 ‡ | 1/2012 | Mandadi | A61Q 11/00 424/52 |
| 2012/0135848 A1 | 5/2012 | Beall et al. | |
| 2012/0317735 A1 | 12/2012 | Gonzales et al. | |
| 2012/0321567 A1 | 12/2012 | Gonzales et al. | |
| 2013/0011446 A1 | 1/2013 | Depaula | |
| 2013/0266625 A1 | 10/2013 | Benita et al. | |
| 2014/0000891 A1 ‡ | 1/2014 | Mahoney | C09K 8/62 166/28 |
| 2014/0026916 A1 | 1/2014 | Havens et al. | |
| 2014/0135202 A1 | 5/2014 | Ritzberger et al. | |
| 2014/0186274 A1 | 7/2014 | Hodgkinson | |
| 2014/0193499 A1 | 7/2014 | Da et al. | |
| 2014/0212469 A1 | 7/2014 | Rahaman et al. | |
| 2014/0219941 A1 ‡ | 8/2014 | Takekawa | A61K 8/022 424/63 |
| 2014/0228196 A1 | 8/2014 | Ritzberger et al. | |
| 2014/0271913 A1 | 9/2014 | Pomrink et al. | |
| 2014/0349831 A1 | 11/2014 | Cornejo et al. | |
| 2014/0370464 A1 | 12/2014 | Kounga et al. | |
| 2015/0087493 A1 | 3/2015 | Ritzberger et al. | |
| 2015/0104655 A1 * | 4/2015 | Kim | C03C 3/097 65/17.6 |
| 2015/0231042 A1 | 8/2015 | Gonzales et al. | |
| 2015/0239772 A1 | 8/2015 | Baker et al. | |
| 2015/0265509 A1 | 9/2015 | Zhang et al. | |
| 2015/0274581 A1 | 10/2015 | Beall et al. | |
| 2015/0299031 A1 | 10/2015 | Ritzberger et al. | |
| 2015/0374589 A1 | 12/2015 | Rampf et al. | |
| 2016/0060159 A1 | 3/2016 | Kim et al. | |
| 2016/0102010 A1 | 4/2016 | Beall et al. | |
| 2016/0145567 A1 | 5/2016 | Henry et al. | |
| 2016/0340239 A1 ‡ | 11/2016 | Propster | A61K 6/818 |
| 2017/0086877 A1 | 3/2017 | Moffarah et al. | |
| 2017/0274118 A1 | 9/2017 | Nazhat et al. | |
| 2017/0340527 A1 | 11/2017 | Chang et al. | |
| 2017/0340666 A1 ‡ | 11/2017 | Deng | C03C 4/0014 |
| 2017/0341975 A1 | 11/2017 | Gross et al. | |
| 2017/0342382 A1 | 11/2017 | Deng et al. | |
| 2017/0342383 A1 | 11/2017 | Deng et al. | |
| 2017/0349876 A1 | 12/2017 | Deng et al. | |
| 2017/0354755 A1 | 12/2017 | Weinberger et al. | |
| 2019/0048318 A1 | 2/2019 | Deng et al. | |
| 2019/0060523 A1 ‡ | 2/2019 | Bakry | A61C 5/00 |

FOREIGN PATENT DOCUMENTS

| | | |
|---|---|---|
| CN | 1032265 A | 4/1989 |
| CN | 1054055 A | 8/1991 |
| CN | 1155844 A | 7/1997 |
| CN | 1213355 A | 4/1999 |
| CN | 1325291 A | 12/2001 |

(56) References Cited

FOREIGN PATENT DOCUMENTS

| | | | |
|---|---|---|---|
| CN | 1615280 A | 5/2005 | |
| CN | 1838936 A | 9/2006 | |
| CN | 101018573 A | 8/2007 | |
| CN | 101407373 A | 4/2009 | |
| CN | 101500622 A | 8/2009 | |
| CN | 101596326 A | 12/2009 | |
| CN | 101704632 A | 5/2010 | |
| CN | 101808955 A | 8/2010 | |
| CN | 102421716 A | 4/2012 | |
| CN | 102430149 A | 5/2012 | |
| CN | 102526797 A | 7/2012 | |
| CN | 103172263 A | 6/2013 | |
| CN | 103449725 A | 12/2013 | |
| CN | 103930086 A | 7/2014 | |
| CN | 103979796 A | 8/2014 | |
| CN | 104039729 A | 9/2014 | |
| CN | 104108883 A | 10/2014 | |
| CN | 104379113 A | 2/2015 | |
| CN | 104736126 A | 6/2015 | |
| CN | 104876439 A | 9/2015 | |
| CN | 105236745 A | 1/2016 | |
| CN | 105819697 A | 8/2016 | |
| CN | 107028770 A | 8/2017 | |
| DE | 10214273 A1 | 10/2003 | |
| DE | 102005026269 A1 | 12/2006 | |
| EP | 0583791 A1 ‡ | 2/1994 | |
| EP | 0885855 A2 | 12/1998 | |
| EP | 0935526 A1 | 8/1999 | |
| EP | 1116698 A1 | 7/2001 | |
| EP | 1123072 A1 | 8/2001 | |
| EP | 1233721 A1 | 8/2002 | |
| EP | 1452496 A1 ‡ | 9/2004 | |
| EP | 1580172 A2 | 9/2005 | |
| EP | 1021148 1021 B1 ‡ | 5/2008 | |
| EP | 2868634 A1 | 5/2015 | |
| EP | 3095436 A1 | 11/2016 | |
| HU | 0302501 A2 | 1/2006 | |
| HU | 227595 B1 ‡ | 9/2011 | |
| HU | 0227595 B1 | 9/2011 | |
| JP | 2001-010843 A | 1/2001 | |
| JP | 3306811 B2 | 7/2002 | |
| JP | 2004359754 A ‡ | 12/2004 | ............ C03C 3/066 |
| JP | 2005-053776 A | 3/2005 | |
| JP | 2005-255517 A | 9/2005 | |
| JP | 2007001846 A ‡ | 1/2007 | ............ C03C 4/20 |
| JP | 2007039269 A ‡ | 2/2007 | ............ C03C 3/064 |
| JP | 2015-504399 A | 2/2015 | |
| JP | 2015-505786 A | 2/2015 | |
| JP | 2015-509016 A | 3/2015 | |
| JP | 2015-525180 A | 9/2015 | |
| KR | 10-2007-0081952 A | 8/2007 | |
| KR | 10-0781952 B1 | 12/2007 | |
| KR | 10-2013-0112422 A | 10/2013 | |
| KR | 20130112433 A ‡ | 10/2013 | ............ C03C 13/00 |
| WO | 87/07256 A1 | 12/1987 | |
| WO | WO-1991012032 A1 ‡ | 8/1991 | |
| WO | WO-1997018171 A1 ‡ | 5/1997 | |
| WO | WO-9727148 A1 ‡ | 7/1997 | |
| WO | 97/27884 A1 | 8/1997 | |
| WO | 98/08672 A1 | 3/1998 | |
| WO | WO-9815263 A2 ‡ | 4/1998 | ........... A61K 9/1647 |
| WO | WO-1999062835 A1 ‡ | 12/1999 | |
| WO | 00/15167 A1 | 3/2000 | |
| WO | 01/34060 A1 | 5/2001 | |
| WO | 2006/072394 A1 | 7/2006 | |
| WO | 2007/022264 A2 | 2/2007 | |
| WO | 2007/141978 A1 | 12/2007 | |
| WO | 2008/000888 A2 | 1/2008 | |
| WO | 2011/084572 A2 | 7/2011 | |
| WO | 2011/141896 A1 | 11/2011 | |
| WO | 2012/091201 A1 | 7/2012 | |
| WO | 2012/137158 A1 | 10/2012 | |
| WO | 2014/015240 A1 | 1/2014 | |
| WO | 2014/052973 A1 | 4/2014 | |
| WO | 2014/095198 A1 | 6/2014 | |
| WO | WO-2014159240 A1 ‡ | 10/2014 | |
| WO | WO-2015034860 A1 ‡ | 3/2015 | |
| WO | 2015/123049 A1 | 8/2015 | |
| WO | 2015/200017 A1 | 12/2015 | |
| WO | 2017/205589 A1 | 11/2017 | |

OTHER PUBLICATIONS

Da Vari, "Dentin Hypersensitivity: Etiology, Diagnosis and Treatment, a Literature Review," J Dent (Shiraz), 2013,14(3): 136-145).‡

De Kerchove et al., "Formation of Polysaccharide Gel Layers in the Presence of Ca2+ and K + Ions: Measurements and Mechanisms", Biomacromolecules 2007, 8,113-121.‡

Coradin et al; "Silica-Alginate Composites for Microencapsulation" Applied Microbiology and Biotechnology, 61(5-6) pp. 429-434 (2003).‡

Copeland et al; "Microbeads: An Emerging Water Quality Issue", Retrieved From fas.org, Jul. 20, 2015, 2 Pgs.‡

Bertling, et al., "Hollow Microspheres". Chem Eng Technol, 2004, 27: 829-837.‡

Budov, "Hollow Glass Microspheres. Use, Properties and Technology (Review Article)", Glass Ceram, 1994, 51: 230-235.‡

Brown et al; "Effect of Borate Glass Composition on Its Conversion to Hydroxyapatite and on the Proliferation of MC3T3-E1 Cells"; Journal of Biomedical Materials Research Part A 88, No. 2, (2009): 392-400.‡

American Type Culture Collection, Product Sheet MC3T3E1, Subclone 14(ATCC@ CRL2594 TM), p. 1-3, Aug. 2014.‡

Apel et al., "Influence of ZrO2 on the Crystallization and Properties of Lithium Disilicate Glass-Ceramics Derived From a Multi-Component System", J Eur Ceram Soc, 2007,27:1571-1577.‡

Ahmed et al; "Processing, Characterisation and Biocompatibility of Iron-Phosphate Glass Fibres for Tissue Engineering", Biomaterials, 25, (2004), 3223-3232.‡

Kaklamani et al; "Mechanical Properties of Alginate Hydrogels Manufactured Using External Gelation", J. MeECH Beh. Biomed. Mater., 2014, pp. 135-142 (Year: 2014).‡

"Azo Materials, ""Silicon Dioxide"", accessed from: ""https://www.azom.com/properties.aspx?Articel D=1114"", accessed on Feb. 19, 2019,pp. 1-4 (Year: 2019)".‡

Maestrelli et al; "Development of Enteric-Coated Calcium Pectinate Microspheres Intended for Colonic Drug Delivery", Eur. J. Pharm. and Biopharm., 2008, pp. 508-518 (Year: 2008).‡

Buchilin et al; "Crystallization-Controlled Pore Retention in Calcium-Phosphate Glassceramics From Powder Sintering of CaO—P205—B203-AI203-TiO2—ZrO2 Glass"; Journal of Non-Crystalline Solids; 373-374 (2013) pp. 42-50.‡

Zheng et al; "Characteristics and Biocompatibility of Na20—K20—CaO—MgO—SrO—B203—P205 Borophosphate Glass Fibers"; Journal of Non-Crystalline Solids; 358 (2012) 387-391.‡

Sharmikn et al; "Effect of Boron Additiona on the Thermal, Degradation, and Cytocompatibility Properties of Phosphate-Based Glasses"; Biomed Research Internaitonal; vol. 2013; Article ID 902427; 12 Pages.‡

Abo-Naf et al; "In Vitro Bioactivity Evaluation, Mechanical Properties and Microstructural Characterization of Na20—CaO—B203—P205 Glasses"; Spectrochimica Acta Part A: Molecular and Biomolecular Spectroscopy; 144 (2015) pp. 88-98.‡

Zahid et al; "Biological Behavior of Bioactive Glasses and Their Composites" ; RSC Adv., 2016, 6 pp. 70197-70214.‡

Ogonczyk et al. "Microfluidic formulation of pectin microbeads for encapsulation and controlled release of nanoparticles," Biomicrofluidics, 2011, pp. 1-12.‡

Gunter et al. "Calcium pectinate gel beads obtained from callus cultures pectins aspromising systems for colon-targeted drug delivery," Carbohydrate Polymers, 2016, pp. 490-499.‡

Andersson et al. "In vivo behaviour of glasses in the SiO2—Na2O—CaO—P2O5—Al2O3—B2O3 system" , J. Mat. Sci: Materials in Medicine (1990) 1: pp. 219-227.‡

Ning et al., "Food Biochemistry" South China University of Technology Press, Edition 1, 1995, 9 pages (5 pages of English Translation and 14 pages of Original Document).

(56) References Cited

OTHER PUBLICATIONS

Peddi et al; "Bioactive Borate Glass Coatings for Titanium Alloys", J. Mater. Sci: Mater. Med., (2008), 19, p. 3145-3152.
Pires et al; "The Role of Alumina in Aluminoborosilicate Glasses for Use in Glass-Ionomer Cements"; J. Mater. Chem, 19 (2009) pp. 3652-3660.
Rahaman et al; "Bioactive Glass in Tissue Engineering", Acta Biomaterialia, 7, (2011), 2355-2373.
Ramanujan, Book Chapter 17, Magnetic Particles for Biomedical Applications, R. Narayan (ed.), Biomedical Materials, DOI 10.1007/978-0-387-84872-3 17, C Springer Science+Business Media, LLC 2009, pp. 477-491.
Sglavo; "Chemical Strengthening of Soda Lime Silicate Float Glass: Effect of Small Differences in the KNO3 Bath," Int J Appl Glass Sci, 2015, 6: 72-82.
Simhan; "Chemical Durability of ZrO2 Containing Glasses"; Journal of Non-Crystalline Solids; 54 (1983) 335-343.
Singh et al; "Characterization of SiO2—Na2O—Fe2O3—CaO-P2O5—B2O3 Glass Ceramics"; Journal of Materials Science: Materials in Medicine, 10(8) pp. 481-484. (1999).
Strassler et al; Dentinal Hypersensitivity: Etiology, Diagnosis and Management; 9 Pages; Date Unknown; www.indeedce.com.
Succaria et al; "Prescribing a Dental Ceramic Material: Zirconia vs Lithium-Disilicate"; The Saudi Dent J, 2011, 23: 165-166.
Wallenberger et al; "The Liquidus Temperature; Its Critical Role in Glass Manufacturing"; International Journal of Applied Glass Science 1 [2] (2010) pp. 151-163.
Xiao et al; "Hollow Hydroxyapatite Microspheres: A Novel Bioactive and Osteoconductive Carrier for Controlled Release of Bone Morphogenetic Protein-2 in Bone Regeneration", Acta Biomater. Sep. 2013; 9(9): 8374-8383.
Yao et al; "In Virto Bioactive Characteristics of Borate-Based Glasses With Controllable Degradation Behavior"; J. Am. Ceram. Soc.; 90 [1]; 303-306 (2007).
Yin et al; "Effect of ZrO2 on the Bioactivity Properties of Gel-Derived CaO—P2O5—SiO2—SrO Glasses"; Ceramics International; 43 (2017) pp. 9691-9698.
Yue et al; "Fiber Spinnability of Glass Melts"; International Journal of Applied Glass Science; (2016) pp. 1-11.
Zhang et al; "Chipping Resistance of Graded Zirconia Ceramics for Dental Crowns"; J Dent Res, 2012, 91:311-315.
G. Jagan Mohini et, al., "Studies on influence of aluminium ions on the bioactivity of B2O3—SiO2—P2O5—Na2O—CaO glass system by means of spectroscopic", Applied Surface Science, vol. 287, 2013, pp. 46-53.
Karem Noris-Suarez et, al., "Osteoblastic cells biomineralized on bioactive glass and glass-ceramics of the SiO2.Na2O.CaO.K 2O.Mg O.P2O5 system modified with Al2O3 and B2O3", Journal of Ceramic Processing Research, vol. 11, No. 2, 2020, 9 pages.
Ricardo A. Pires et, al., "The role of alumina in aluminoborosilicate glasses for use in glass-inomercementa", Journal of Materials Chemistry, vol. 19, 2009, pp. 3652-3660.
A. Saranti, et al., "Bioactive glasses in the system CaO—B2O3—P2O5; preparation, structural study and in vitro evaluation." Journal of Non-Crystalline Solids 352, No. 5 (2006): 390-398.
Antonio Tilocca et al., "Structural Effects of Phosphorus Inclusion in Bioactive Silicate Glasses", J. Phys. Chem. B., 2007, 111, 14256-14264.
C. M. Rochman,et al., Scientific evidence supports a ban on microbeads, Environ Sci & Tech, 2015, 49: 10759-10761.
Dutra Zanotto, "A bright future for glass-ceramics", American Ceramic Society Bulletin, vol. 89, No. 8, pp. 19-27, 2010.
E.A. Abou Neel.et al., "Effect of iron on the surface, degradation and ion release properties of phosphate-based glass fibres." Acta Biomaterialia 1, No. 5 (2005): 553-563.
El-Kheshen et al.; "Effect of Al2O3 Addition On Bioactivity, Thermal and Mechanical Properties of Some Bioactive Glasses"; Ceramics Int. (2008) 34: 1667-1673 (Year: 2008).

F. Jay Murray, Issues in Boron Risk Assessment: Pivotal Study, Uncertainty Factors, and ADIs, The Journal of Trace Elements in Experimental Medicine 9, No. 4 (1996): 231-243.
Fabienne C. Raszewski et al., Methods For Producing Hollow Glass Microspheres, Savannah River National Laboratory, Aiken, SC 29808, Mar. 2016.
Fendall et al; "Contributing to Marine Pollution by Washing Your Face: Microplasitcs in Facial Cleansers"; Marine Pollution Bulletin 58 (8): 1225-1228 (2009)).
Forsback et al; "Mineralization of Dentin Induced by Treatment With Bioactive Glass S53P4 In Vitro"; Acta Odontol Scand, 62 (2004); pp. 14-20.
Franks et al; "The Effect of MgO on the Solubility Behaviour and Cell Proliferation in a Quaternary Soluble Phosphate Based Glass System", J. of Mate. Science: Materials in Medicine, 13, (2002), 549-556.
Fu et al; "Bioactive Glass Innovations Through Academia-Industry Collaboration"; International Journal of Applied Glass Science, 7 [2], (2016) pp. 139-146.
Fu et al; "Bioactive Glass Scaffolds for Bone Tissue Engineering: State of the Art and Future Perspectives", Materials Science and Engineering, C 31, (2011), 1245-1256.
Fu et al; "Hollow Hydroxyapatite Microspheres as a Device for Controlled Delivery of Proteins"; J Mater Sci: Mater Med., 2011;22:579-91.
Fu et al; "Nature-Inspired Design of Strong, Tough Glass-Ceramics," MRS Bulletin, 2017, 42:220-225.
Fu et al; "Silicate, Borosilicate, and Borate Bioactive Glass Scaffolds With Controllable Degradation Rate for Bone Tissue Engineering Applications. I. Prepareation and in Vitro Degradation"; Journal of Biomedical Materials Research A; 2010; vol. 95A; Issue 1; pp. 164-171.
Fuat Topuz, et al., Magnesium ions and alginate do form hydrogels: a rheological study, Soft Matter, Aug. 2012, 4877-4881.
Gorustovich et al. "Osteoconductivity of strontium-doped bioactive glass particles: A histomorphometric study in rats," J Biomed Materials Res. Part A (2010) 92A: pp. 232-237.
Graham, "High-Sensitivity Manetization Measurements", J. Mater. Sci. Technol., vol. 16, No. 2, 2000, p. 97-101.
Gy, "Ion Exchange for Glass Strengthening," Mater Sci EHG B, 2008, 149: 159-165.
Han et al; "In Vivo Remineralization of Dentin Using an Agarose Hydrogel Biomimetic Mineralization System"; Nature, Scientific Reports; (2017); 9 Pages.
Harianawala et al. "Biocompatibility of Zirconia", J Adv Med Deni Sci Res 4(3) 2016, pp. 35-39.
Hench; "Bioceramics", J. Am. Ceram. Soc., 81, (7), 1705-1728 (1998).
Hiorth et al; "Immersion Coating of Pellets With Calcium Pectinate and Chitosan"; International Journal of Pharmaceutics 308 (2006) 25-32.
Holand et al; "A Comparison of the Microstructure and Properties of the IPS EmpressT2 and the IPS Empresst Glass-Ceramics"; J Biomed Mater Res (Appl Biomater), 2000, 53: 297-303.
Huang et al; "Kinetics and Mechanisms of the Conversion of Silicate (45S5), Borate and Borosilicate Glasses to Hydroxyapatite in Dilute Phosphate Solutions," J Mater Sci Mater Med 2006, 17: 583-596.
Huipin Yuan, et al., "Osteoinduction by calciumphosphate biomaterials", Journal of Materials Science: Materials in Medicine 9 (1998) 723-726.
Imogen E. Napper et al., Characterisation, quantity and sorptive properties of microplastics extracted from cosmetics, Marine Pollution Bulletin, vol. 99, Issues 1-2, Oct. 15, 2015, pp. 178-185.
International Search Report and Written Opinion of the International Searching Authority; PCT/US2018/062713; dated May 8, 2019; 17 Pages; European Patent Office.
Jacoby; "New Applications for Glass Emerge," Chem. Eng. News, 90 [25] 34-36 (2012).
Jianxi Lu, et al., The Biodegradation Mechanism of Calcium Phosphate Biomaterials in Bone, Journal of Biomedical Materials Research, Aug. 2002, 63(4): 408-412.

(56) References Cited

OTHER PUBLICATIONS

Jonathan C. Knowles, Phosphate based glasses for biomedical applications, J. Mater. Chem., 2003, 13, 2395-2401.
Jones; "Review of Bioactive Glass: From Hench to Hybrids"; Acta Biomaterialia 9 (2013) pp. 4457-4486.
Kokubo et al; "How Useful is SBF in Predicting In Vivo Bone Bioactivity?"; Biomaterials, 27, (2006), 2907-2915.
Kulal et al; "An In-Vitro Comparison of Nano Hydroxyapatite, Novamin and Proargin Desensitizing Toothpastes—A SEM Study"; Journal of Clinical and Diagnostic Research; 2016; vol. 10 (10) ZC51-ZC54.
Kumaryadav et al; "Development of Zirconia Substituted 1393 Bioactive Glass for Orthopaedic Application"; Oriental Journal of Chemistry; vol. 33, No. 6; (2017) pp. 2720-2730.
L. Hench et al., "Third-Generation Biomedical Materials", Science, vol. 295, Feb. 8, 2002, p. 1016-1017, www.sciencemag.org, Downloaded from www.sciencemag.org on Aug. 5, 2015.
L. Hench, and J. Jones, eds. Biomaterials, artificial organs and tissue engineering. Elsevier, 2005—book.
Lien et al; "Microstructural Evolution and Physical Behavior of a Lithium Disilicate Glass-Ceramic"; Dent Mater 2015, 31: 928-940.
Low et al; "Reduction in Dental Hypersensitivity With Nano-Hydroxyapatite, Potassium Nitrate, Sodium Monoflurophosphate and Antioxidants"; The Open Dentistry Journal; (2015), 9, pp. 92-97.
Marcolongo et al; "Surface Reaction Layer Formation In Vitro on a Bioactive Glass Fiber/Polymeric Composite"; J. Biomed Mater. Res.; (1997); 37, pp. 440-448.
Maziar Montazerian, et al. "History and trends of bioactive glass-ceramics", Journal of Biomedical Materials Research A, 2016, vol. 104A, 1231-1249, 2016 Wiley Periodicals, Inc.
Miglani et al; "Dentin Hypersensitivity: Recent Trends in Management"; J. Conserv. Dent. 2010; 13 (4) pp. 218-224.
Mintatoya et al; "Bioactive Glass Cloth That Propmotes New Bone Formation"; Key Eng. Mater.; (2013) 529-530; pp. 266-269.
Mohini et al; "Studies on Influence of Aluminium Ions on the Bioactivity of $B_2O_3$—$SiO_2$—$P_2O_5$—$Na_2O$—CaO Glass System By Means of Spectroscopic Studies"; Applied Surface Science; 287 (2013) pp. 46-53.
Morch et al; "Effect of $Ca^{2+}$, $Ba^{2+}$, and $Sr^{2+}$ on Alginate Microbeads"; Biomacromolecules 2006, 7, 1471-1480.
Motohiro Uo et al., Properties and cytotoxicity of water soluble $Na_2O$—CaO—$P_2O_5$ glasses, Biomaterials, 19, (1998), 2277-2284.
Neel, et al; "Characterisation of Antibacterial Copper Releasing Degradable Phosphate Glass Fibres." Biomaterials 26, No. 15 (2005): 2247-2254.
Noris-Suarez et al; "Osteoblastic Cells Biomineralized on Bioactive Glass and Glass-Ceramics of the $SiO_2Na_2O.CaO.K_2O.MgO.P_2O_5$ System Modified With $Al_2O_3$ and $B_2O_3$"; Journal of Ceramic Processing Research; vol. 11, No. 2 (2010) pp. 129-137.
Ohgushi et al; Bioceramics vol. 11, Legeros et al, Ed., Proc. 11th Int. Symp. Ceramics. Med. (NY:NY), Nov. 1998, pp. 261-264 (Year 1998).
Liu et al. "The Effect of Novel Fluorapatite Surfaces on Osteoblast-Like Cell Adhesion, Growth, and Mineralization" Tissue Engineering: Part A, vol. 16, No. 9, 2010 (Year: 2010).
Ohgushi et al., "$Al_2O_3$ doped apatite-wollastonite containing glass ceramic provokes osteogenic differentiation of marrow stromal stem cells", J Biomed Mater Re, vol. 44, Issue 4 pp. 381-388, 1998.
Zhao et al., "Mechanism for converting $Al_2O_3$-containing borate glass to hydroxyapatite in aqueous phosphate solution", Acta Biomaterialia, Dec. 10, 2008, vol. 5, No. 4, pp. 1265-1273.
Japanese Patent Application No. 2018561573 Office Action dated Feb. 24, 2021, 14 pages (7 pages of English Translation and 7 pages of Original Document); Japanese Patent Office.
Chinese Patent Application No. 201880077026.2, Office Action dated Mar. 19, 2022, 5 pages of English Translation, Chinese Patent Office.

\* cited by examiner
‡ imported from a related application

CHEMICALLY STRENGTHENED BIOACTIVE GLASS-CERAMICS

CROSS-REFERENCE TO RELATED APPLICATIONS

This application is a Divisional of U.S. application Ser. No. 16/202,786, filed on Nov. 28, 2018, now U.S. Pat. No. 10,857,259, issued Dec. 8, 2020, which claims the benefit of priority under 35 U.S.C. § 119 of U.S. Provisional Patent Application No. 62/591,438, filed Nov. 28, 2017, the contents of both of which are incorporated herein by reference in their entirety.

CROSS REFERENCE TO RELATED APPLICATIONS

The disclosure relates to commonly owned and assigned U.S. Provisional Patent Application Nos.

62/342,384, filed May 27, 2016, entitled "BIOACTIVE ALUMINOBORATE GLASSES";

62/342,377, filed May 27, 2016, entitled "MAGNETIZABLE GLASS CERAMIC COMPOSITION AND METHODS THEREOF";

62/342,381, filed May 27, 2016, entitled "LITHIUM DISILICATE GLASS-CERAMIC COMPOSITIONS AND METHODS THEREOF";

62/342,391, filed May 27, 2016), entitled "BIODEGRADABLE MICROBEADS";

62/342,411, filed May 27, 2016, entitled "BIOACTIVE GLASS MICROSPHERES"; and

62/342,426, filed May 27, 2016, entitled "BIOACTIVE BOROPHOSPHATE GLASSES"; but does not claim priority thereto.

The disclosure also relates, but does not claim priority to, commonly owned and assigned patent applications:

61/941,677, entitled "ANTIMICROBIAL GLASS COMPOSITIONS, GLASSES AND ARTICLES INCORPORATING THE SAME", and 61/941,690, entitled "ANTIMICROBIAL GLASS COMPOSITIONS, GLASSES AND POLYMERIC ARTICLES INCORPORATING THE SAME," both filed Feb. 19, 2014, both mention Cu containing compositions having articles having antimicrobial properties; and Corning patent application Ser. No. 14/623,674, now US Pat Pub. 20150239772, entitled "LOW CRYSTALLINITY GLASS-CERAMICS", which mentions crystallisable glasses and glass-ceramics that exhibit a black color and are opaque.

The present application is also related commonly owned and assigned U.S. Ser. No. Application Nos.:

62/591,423 filed Nov. 28, 2017, entitled "BIOACTIVE GLASS COMPOSITIONS AND METHODS OF TREATING DENTIN HYPERSENSITIVITY";

62/591,446 filed Nov. 28, 2017, entitled "HIGH LIQUIDUS VISCOSITY BIOACTIVE GLASS"; and 62/591,429, filed Nov. 28, 2017, entitled "BIOACTIVE BORATE GLASS AND METHODS THEREOF", filed concurrently herewith, but does not claim priority thereto.

The entire disclosure of each publication or patent document mentioned herein is incorporated by reference.

BACKGROUND

The disclosure relates to chemically strengthened bioactive glass-ceramics, and method of making and using the glass-ceramics.

SUMMARY

In embodiments, the disclosure provides a method of making a glass-ceramic article, including a chemical strengthening process that improves the flexural strength of lithium disilicate glass-ceramics. The glass-ceramic articles can be ion exchanged in, for example, $NaNO_3$ or $KNO_3$ for a suitable time. Both $Li_2O$ and $Na_2O$ ions in the residual glass can be ion exchanged.

In embodiments, the disclosure provides a chemically strengthened bioactive glass-ceramic based on lithium disilicate, apatite, and wollastonite.

In embodiments, the disclosure provides a glass-ceramic article having a flexural strength of over 1000 MPa, which strength can be achieved after ion exchange. The strength is comparable to $ZrO_2$ ceramics.

In embodiments, the disclosure provides an ion-exchanged glass-ceramics having bioactivity that is retained even after the ion-exchange strengthening process.

In embodiments, the disclosure provides glass-ceramic compositions having lithium disilicate as the primary major crystal phase, and at least one of wollastonite, fluorapatite, cristobalite, β-quartz, lithiophosphate, or mixtures thereof as minor phases. The compositions can comprise, for example, 50 to 75% $SiO_2$, 1 to 5% $Al_2O_3$, 0.1 to 10% $B_2O_3$, 5 to 20% $Li_2O$, 0.5 to 5% $Na_2O$, 0 to 4% $K_2O$, 0.5 to 8% $ZrO_2$, and 0.1 to 1.0% $F^-$ (i.e., fluoride ion) (i.e., fluoride ion), based on a 100 wt % total of the composition.

BRIEF DESCRIPTION OF THE DRAWINGS

In embodiments of the disclosure.

DETAILED DESCRIPTION

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

In embodiments, the disclosed method of making and using provide one or more advantageous features or aspects, including for example as discussed below. Features or aspects recited in any of the claims are generally applicable to all facets of the invention. Any recited single or multiple feature or aspect in any one claim can be combined or permuted with any other recited feature or aspect in any other claim or claims.

Definitions

"IOX," "IX," "IOXing," "IOX'ed," "IOX'd," "ion-exchange," "ion-exchanged," "ion-exchanging," or like terms refer to the ion exchange of ions, partially or completely, on at least a portion of the glass or glass-ceramic surface, on one or both sides as specified, with different ions such as an ion having a larger atomic radius compared to the exchanged ions such as $K^+$ ions exchanged (i.e., replacing) for $Na^+$ ions (see also, for example, U.S. Pat. Nos. 3,790,430, and 3,778,335).

"Glass," "glass-ceramic," or like terms can refer to the disclosed glass precursor or the disclosed glass-ceramic product compositions that has been either strengthened or un-strengthened.

"Glass article," "glass-ceramic article," or like terms can refer to any object made wholly or partly of any of the disclosed glass or glass-ceramic compositions.

"Bioactivity Index" "index of bioactivity," "$I_B$," or like terms or symbols refer to, for example, the time for more than 50% of the interface of a specific bioactive material to be bonded by a biological material such as bone, tissue, and like materials. Mathematically, a bioactivity index (according to Hench; see Cao, W., et al., Bioactive Materials, Ceramics International, 22 (1996) 493-507) is, $I_B=100/t_{0.5bb}$, where $t_{0.5bb}$ is the time for more than 50% of a bioactive material's interface, such as an implant, to be bonded by a biological material such as bone, tissue, and like materials, including osteoproductive (Class A having both intracellular and extracellular responses, e.g., 45S5 Bioglass®) and osteoconductive (Class B extracellular response only at interface, e.g., synthetic hydroxyapatite) materials.

"Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, viscosities, and like values, and ranges thereof, or a dimension of a component, and like values, and ranges thereof, employed in describing the embodiments of the disclosure, refers to variation in the numerical quantity that can occur, for example: through typical measuring and handling procedures used for preparing materials, compositions, composites, concentrates, component parts, articles of manufacture, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

"Optional" or "optionally" means that the subsequently described event or circumstance can or cannot occur, and that the description includes instances where the event or circumstance occurs and instances where it does not.

The indefinite article "a" or "an" and its corresponding definite article "the" as used herein means at least one, or one or more, unless specified otherwise.

Abbreviations, which are well known to one of ordinary skill in the art, may be used (e.g., "h" or "hrs" for hour or hours, "g" or "gm" for gram(s), "mL" for milliliters, and "rt" for room temperature, "nm" for nanometers, and like abbreviations).

Specific and preferred values disclosed for components, ingredients, additives, dimensions, conditions, times, and like aspects, and ranges thereof, are for illustration only; they do not exclude other defined values or other values within defined ranges. The composition and methods of the disclosure can include any value or any combination of the values, specific values, more specific values, and preferred values described herein, including explicit or implicit intermediate values and ranges.

Bioactive materials with high strength and toughness are in significant demand for the regeneration of bone and teeth. Glass-ceramics based on lithium disilicate offer desirable mechanical properties, including high body strength and fracture toughness, due to their microstructures of randomly-oriented interlocking crystals. Flexural strength in the range of 300 to 400 MPa is reported for lithium disilicate glass-ceramics (W. Holand, et al., A Comparison of the Microstructure and Properties of the IPS EmpressT2 and the IPS EmpressT Glass-Ceramics, J Biomed Mater Res (Appl Biomater), 2000, 53: 297-303; W. Liena, et al., Microstructural evolution and physical behavior of a lithium disilicate glass-ceramic, Dent Mater 2015, 31: 928-940), which makes them suitable for applications in in the fabrication of single and multiple dental restorations. Furthermore, the superior aesthetics and the ability to form a monolithic structure make lithium disilicate a viable option for dental patients. However, the low flexural strength of lithium disilicate makes them less suitable for applications where stress concentration can be high (see Zhang Y., et al., Chipping resistance of graded zirconia ceramics for dental crowns. J Dent Res, 2012, 91:311-315). In comparison, $ZrO_2$ ceramics are reported to have a flexural strength over 1000 MPa (see Zhang supra., and F. Succaria, et al., Prescribing a dental ceramic material: Zirconia vs lithium-disilicate. *Saudi Dent J*, 2011, 23: 165-166). They can be used as multi-unit bridges for dental restoration. However, the lack of high translucency and the lower ability to match the appearance of natural teeth remain challenges for $ZrO_2$ ceramics in dental restorations (see Succaria, supra.). There is a significant need of glass-ceramics having improved strength while maintaining their: aesthetic attributes, ease in forming, and machine ability.

Glass strengthening by ion exchange (chemical tempering) has been widely used to improve the mechanical strength and product reliabilities in a variety of glass and glass-ceramics (see R. Gy, "Ion exchange for glass strengthening," Mater Sci Eng B, 2008, 149: 159-165; and R. J. Araujo, "Strengthening glass by ion exchange," U.S. Pat. No. 5,674,790A, 1997).—In this process, glass articles are immersed into a molten alkali salt at a temperature below the glass transition to allow the alkali ions from the glass surface to exchange for those from the molten salt. The larger ionic radius of penetrating ions than the ions leaving the glass results in the strengthening of the glasses. As a result, the introduction of surface compression strengthens glasses and effectively reduces the probability of breakage from surface flaws (see V. M. Sglavo, "Chemical strengthening of soda lime silicate float glass: effect of small differences in the $KNO_3$ bath," *Int J Appl Glass Sci*, 2015, 6: 72-82). This strengthening technique has been widely used in glass products including aircraft cockpit windshields, transparent armor, glass container, and information technology devices (cell phones and tablets) (see M. Jacoby, "New Applications for Glass Emerge," Chem. Eng. News, 90 [25] 34-36 (2012)). However, the lithium disilicate phase is not ion exchangeable due to the lack of mobile ions in its microstructure.

In embodiments, the disclosure provides a method for improving the flexural strength of lithium disilicate glass-ceramics through chemically strengthening (ion exchange) of the residual glass phase in the material. The flexural strength of glass-ceramics is more than doubled after ion exchange, which makes the flexural strength of the product glass-ceramic comparable to $ZrO_2$ ceramics. The glass-ceramics have excellent bioactivity.

In embodiments, the disclosure provides a glass-ceramic composition, comprising: a first crystalline phase and a second crystalline phase, in combination, comprise a source of:
50 to 75 wt % $SiO_2$,
1 to 5 wt % $Al_2O_3$,
0.1 to 10% $B_2O_3$,
5 to 20 wt % $Li_2O$,
0.5 to 5 wt % $Na_2O$,
0.1 to 4% $K_2O$,
0.5 to 6 wt % $P_2O_5$
0.5 to 8% $ZrO_2$, and
0.1 to 1.0 wt % $F^-$, based on a 100 wt % total of the composition.

In embodiments, the disclosure provides a glass-ceramic composition where the source is:
50 to 70 wt % $SiO_2$,
1 to 4 wt % $Al_2O_3$,
0.1 to 4% $B_2O_3$,
6 to 18 wt % $Li_2O$,
1 to 4 wt % $Na_2O$,
0.1 to 3% $K_2O$,
1 to 5 wt % $P_2O_5$
1 to 6% $ZrO_2$, and
0.1 to 1.0 wt % $F^-$, based on a 100 wt % total of the composition.

In embodiments, the glass-ceramic composition can further comprise having composition particles that have ion-exchanged surfaces having a reduced lithium ion ($Li^+$) concentration and having at least one of an elevated sodium ($Na^+$) concentration, an elevated potassium ($K^+$) concentration, or an elevated concentrations of lithium ion ($Li^+$) and sodium ion ($Na^+$).

In embodiments, the glass-ceramic composition can have a first crystalline phase that comprises of from 50 to 99 wt % and a second crystalline phase that comprises of from 1 to 50 wt % based on a 100 wt % total of the composition.

In embodiments, the disclosure provides a glass-ceramic composition, comprising: a first crystalline phase and a second crystalline phase, in combination, comprising:
55 to 65 wt % $SiO_2$,
2 to 4 wt % $Al_2O_3$,
8 to 16 wt % $Li_2O$,
1 to 4 wt % $Na_2O$,
0.1 to 2% $K_2O$,
2 to 5 wt % $P_2O_5$
1 to 5% $ZrO_2$, and
0.1 to 1.0 wt % $F^-$, based on a 100 wt % total of the composition.

In embodiments, the disclosure provides a glass-ceramic composition where the composition is free of $B_2O_3$.

In embodiments, the disclosure provides a glass-ceramic comprising:
50 to 75 wt % $SiO_2$,
1 to 5 wt % $Al_2O_3$,
0.1 to 10% $B_2O_3$,
5 to 20 wt % $Li_2O$,
0.5 to 5 wt % $Na_2O$,
0.1 to 4% $K_2O$,
0.5 to 6 wt % $P_2O_5$
0.5 to 8% $ZrO_2$, and
0.1 to 1.0 wt % $F^-$, based on a 100 wt % total of the composition.

In embodiments, the source or precursor batch composition has the same composition as the glass-ceramic. The bulk composition is essentially still the same composition after ion exchange. Only the surface composition changes as a result of surface ion exchange.

In embodiments, the glass-ceramic composition as an article has a flexural strength of from 300 to 2,000 MPa.

In embodiments, the disclosure provides a method of making a glass-ceramic article comprising:
forming a melt mixture of a source of:
50 to 75 wt % $SiO_2$,
1 to 5 wt % $Al_2O_3$,
0.1 to 10% $B_2O_3$,
5 to 20 wt % $Li_2O$,
0.5 to 5 wt % $Na_2O$,
0.1 to 4% $K_2O$,
0.5 to 6 wt % $P_2O_5$
0.5 to 8% $ZrO_2$, and
0.1 to 1.0 wt % $F^-$, based on a 100 wt % total of the composition to form a glass-ceramic article; and
at least one chemical strengthening of the resulting glass-ceramic article.

In embodiments, the at least one chemical strengthening of the resulting glass-ceramic article can be accomplished by ion exchanging in $NaNO_3$, in $KNO_3$, or in a mixture thereof, for a suitable time, to reduce the concentration of lithium ion, sodium ion, or both, on the surface of the glass-ceramic article.

In embodiments, the article can be, for example, a suitable geometry or form factor, for example, a pattie, a dimensioned portion cut from a pattie, for example, a disc, a monolith, a plurality of particles, a drawn sheet, and like form factors, or combinations thereof.

In embodiments, the article has bioactivity before ion-exchanging.

In embodiments, the article has bioactivity after ion-exchanging.

The present disclosure is advantaged in several aspects, including for example:
lithium disilicate glass-ceramics having strengths comparable to $ZrO_2$ ceramics can be achieved after ion exchange; and
the ion exchange process does not compromise the bioactivity of the disclosed glass-ceramics.

In embodiments, the disclosure provides a method of making lithium disilicate glass-ceramics that includes a chemically strengthening (e.g., ion exchange), and results in a glass-ceramic having increased flexural strength. The flexural strength of the disclosed glass-ceramic compositions is more than doubled after ion-exchange, e.g., to over 1000 MPa, which is comparable to that of $ZrO_2$ ceramics. The high flexural strength enables the use of the disclosed lithium disilicate glass-ceramic compositions in multi-unit bridges for dental restoration. Unexpectedly, the disclosed chemical strengthening step does not impact the bioactivity of the resulting strengthened lithium disilicate glass-ceramic. The major phase in the disclosed glass-ceramics is lithium disilicate, and minor phases can be, for example, fluoroapatite and wollastonite. Both fluoroapatite and wollastonite are beneficial to the attachment and growth of osteoblastic cells.

In embodiments, the precursor glasses can comprise, for example, 50 to 75% $SiO_2$, 1 to 5% $Al_2O_3$, 0.1 to 10% $B_2O_3$, 5 to 20% $Li_2O$, 0.5 to 5% $Na_2O$, 0 to 4% $K_2O$, 0.5 to 8% $ZrO_2$, and 0.1 to 1.0% $F^-$ based on the total weight percentage of 100 wt % (see Table 1).

Figure 1:
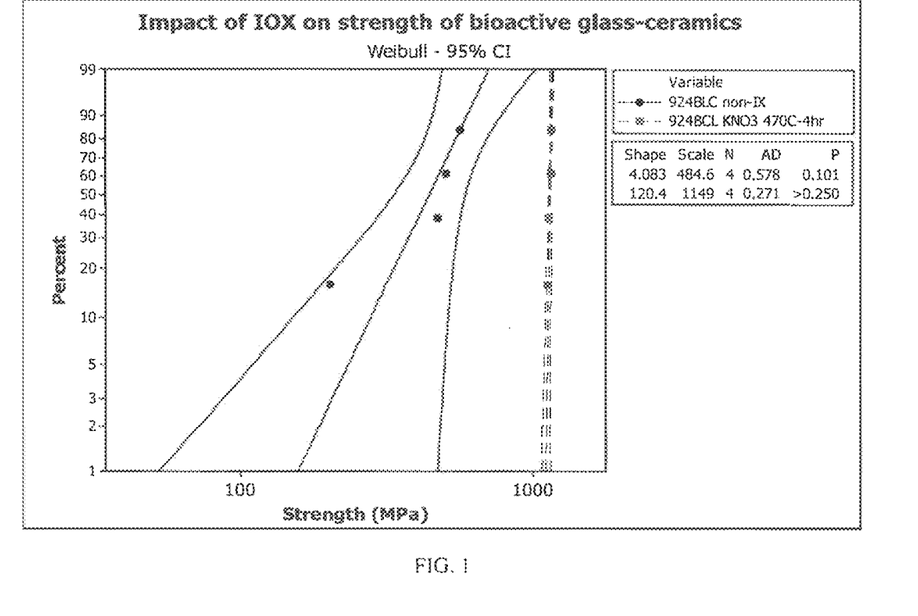
FIG. 1 shows a comparison of flexural strength of a lithium disilicate glass-ceramic (i.e., Example composition 9) before (dots) and after (squares) ion exchange.

In embodiments, the flexural strength of the lithium disilicate glass-ceramics can be improved by, for example, a factor of two as a result of the ion exchange treatment. By ion exchanging in KNO₃ at 470° C. for 4 hr, the flexural strength of an example glass-ceramic Composition 9 was increased from 485 MPa to 1150 MPa (squares). In embodiments, the mechanical reliability (i.e., the probability of success: Reliability=1−Probability of Failure) was also improved as measured by an increase of the Weibull modulus (a dimensionless parameter of the Weibull distribution, which is used to describe variability in measured material strength of brittle materials), from 4 to over 120 (see FIG. 1). The flexural strength of the ion-exchanged glass-ceramic of the disclosure (e.g., 270) was much higher than a commercially available bioactive glass (i.e., 45S5 Bioglass®) (200), glass-ceramics (Biovert (210), A/W (230) (see L. L. Hench, "Bioceramics," J Am Ceram Soc, 1998, 81: 1705-1728), IPS e.max (240), and IPS e.max CAD (250) (Fu, et al., "Nature-inspired design of strong, tough glass-ceramics," MRS Bulletin, 2017, 42:220-225), or ceramics HA (220). The flexural strength of the ion-exchanged glass-ceramic of the disclosure (e.g., 1150) was comparable to ZrO₂ ceramics (1000) (FIG. 2)(Fu, et al., MRS Bulletin, supra.). The flexural strength of the disclosed glass-ceramic compositions make them suitable biomaterial candidates for use in, for example, dental multi-unit bridges.

FIGS. 3A to 3I show a cell culture study on glass-ceramics before (3A to 3C) and after ion-exchanging ("IOX") (3D to 3F). Cell morphology is evident for the un-ion-exchanged Example Composition 9 after: a) one day (3A), b) four days (3B), and c) seven days (3C). A similar cell morphology was observed on IOX'd parts (KNO₃, 470° C. for 4 hr) after: d) one day (3D); e) four days (3E); and f) seven days (3F). Comparable cell morphology was seen on TCT culture plates after: g) one day (3G); h) four days (3G); and i) seven days (3I). A MC3T3 cell line was used for cell culture test.

In embodiments, the bioactivity of the disclosed lithium disilicate containing articles was substantially or entirely retained after an ion-exchange strengthening step. Cell attachment and cell growth were clearly observed on the surfaces of the disclosed glass-ceramic articles with and without ion-exchange (FIG. 3). No visible difference in cell attachment at day 1, and cell expansion at day 4 and day 7 was observed between the non-ion-exchanged and the ion-exchanged materials. The cell morphology was also similar to those cultured on a Tissue Culture Treated® (TCT) culture wells. "TCT" refers to a tissue culture treated microplate substrate available from Corning, Inc®.

In embodiments, both Li₂O and Na₂O in residual glass phase can be ion exchanged to create a compressive stress layer in the surface of the ware to further improve mechanical strength.

Tables 1 and 2 list examples of the as-batched compositions. The ceramming cycle for each of the samples 1 to 15 was 700° C. at 2 hr and 800° C. at 4 hr.

TABLE 1

Examples of As-batched compositions.[2]

| Oxides (wt %) | 1 | 2 | 3 | 4 | 5 | 6 | 7 | 8 |
|---|---|---|---|---|---|---|---|---|
| SiO₂ | 70 | 65 | 60 | 55 | 60 | 60 | 70 | 65 |
| B₂O₃ | 0 | 0 | 0 | 0 | 0 | 0 | 0 | 0 |
| Al₂O₃ | 2.5 | 2.5 | 2.5 | 2.5 | 2.5 | 2.5 | 2.5 | 2.5 |
| Li₂O | 12 | 12 | 12 | 12 | 15 | 12 | 12 | 12 |
| Na₂O | 2 | 2 | 2 | 2 | 2 | 2 | 2 | 2 |
| CaO | 6 | 6 | 6 | 6 | 6 | 6 | 6 | 6 |
| P₂O₅ | 4 | 4 | 4 | 4 | 4 | 4 | 4 | 4 |
| ZrO₂ | 2 | 2 | 2 | 2 | 2 | 4 | 2 | 2 |
| F⁻ | 0 | 0 | 0 | 0 | 0 | 0 | 0.5 | 0.5 |
| Phase assemblage[1] | A | A | A | B | C | D | E | E |
| Flexural strength (MPa) | — | — | — | — | — | — | 504 | 407 |
| Fracture toughness (MPa · m^0.5) | — | — | — | — | — | — | 1.8 | 1.9 |

TABLE 2

Examples of As-batched compositions.[2]

| Oxides (wt %) | 9 | 10 | 11 | 12 | 13 | 14 | 15 |
|---|---|---|---|---|---|---|---|
| SiO₂ | 60 | 55 | 60 | 60 | 60 | 60 | 60 |
| B₂O₃ | 0 | 0 | 0 | 0 | 2 | 4 | 6 |
| Al₂O₃ | 2.5 | 2.5 | 2.5 | 2.5 | 2.5 | 2.5 | 2.5 |
| Li₂O | 12 | 12 | 15 | 12 | 12 | 12 | 12 |
| Na₂O | 2 | 2 | 2 | 2 | 2 | 2 | 2 |
| CaO | 6 | 6 | 6 | 6 | 6 | 6 | 6 |
| P₂O₅ | 4 | 4 | 4 | 4 | 4 | 4 | 4 |
| ZrO₂ | 2 | 2 | 2 | 4 | 2 | 2 | 2 |
| F⁻ | 0.5 | 0.5 | 0.5 | 0.5 | 0.5 | 0.5 | 0.5 |
| Phase assemblage[1] | I | G | J | H | I | I | I |
| Flexural strength (MPa) | 485 | 303 | — | — | — | — | — |
| Fracture toughness (MPa · m^0.5) | 2.2 | 2.2 | — | — | — | — | — |

1. Phase assemblage key for compositions of Tables 1 and 2:
    A=Lithium disilicate, cristobalite, wollastonite, β-quartz, lithiophosphate.
    B=Lithium disilicate, wollastonite, lithiophosphate.
    D=Lithium disilicate, β-quartz, lithiophosphate.
    E=Lithium disilicate, cristobalite, fluorapatite, β-quartz.
    G=Lithium disilicate, fluorapatite, lithium metasilicate, β-quartz.
    H=Lithium disilicate, fluorapatite, β-quartz.
    I=Lithium disilicate, fluorapatite, β-quartz, lithiophosphate.
    J=Lithium disilicate, lithium metasilicate, fluorapatite, β-quartz.
2. Sample Appearance: Samples of Examples 1 to 8 and 10 to 15 were translucent white; Example 9 was translucent/semi-transparent white.

Raw materials, equipment, or both, used to produce the compositions of the present disclosure, can introduce certain impurities or components that are not intentionally added, and can be present in the final glass composition. Such materials can be present in the disclosed compositions in minor amounts and are referred to as "tramp materials."

Disclosed compositions can comprise the tramp materials, typically in trace amounts. Similarly, "iron-free," "sodium-free," "lithium-free," "zirconium-free," "alkali earth metal-free," "heavy metal-free," or like descriptions, mean that the tramp material was not purposefully added to the composition, but the composition may still comprise iron, sodium, lithium, zirconium, alkali earth metals, or heavy metals, etc., but in approximately tramp or trace amounts.

Unless otherwise specified, the concentrations of all constituents recited herein are expressed in terms of weight percent (wt %).

EXAMPLES

The following Examples demonstrate making, use, and analysis of the disclosed compositions and methods in accordance with the above general procedures.

Example 1

Preparation of Actual Example Glass-Ceramic Compositions Example Glass-Ceramic Compositions 1 to 15 listed in Tables 1 and 2, and their respective source batch materials in the indicated amounts, including for example, silica, boric acid, alumina, lithium carbonate, sodium carbonate, limestone, spodumene, aluminum metaphosphate, were individually combined and melted in an electric furnace. Prior to melting, the batch source materials were vigorously mixed in a plastic jar using a Turbula® mixer. Then the mixtures were transferred to a platinum crucible with an internal volume of approximately 650 cc and heated at 1350° C. for 6 hr, and then the glass melt was poured on a steel plate, and annealed at 500° C. to produce an article in the form of a pattie. Alternatively, the glass melt can be drawn into a glass-ceramic sheet article or a fiber article. The resulting article was ion-exchanged before or after further processing and as mentioned in Example 2.

Example 2

Further Processing of the Pattie Article of the Bioactive Composition of Example 1 The pattie or sheet of Example 1 was further processed into other useful forms, for example: cutting to produce a portion cut from a pattie such as a disc, or a monolith to desired dimensions; crushing to produce a plurality of particles by, for example, any suitable crushing or pulverizing equipment. The resulting article was ion-exchanged before or after the further processing mentioned here.

Example 3

Method of Attachment and Growth of Bone Cells with the Bioactive Composition of Example 1 Ion exchanged glass ceramic discs (12.5 mm in diameter×1 mm thick), obtained from disc cutting and ion-exchange mentioned in Example 2 and described further below, were placed into wells of 24 well microplates. MC3T3 cells were seeded to each well at a density of 10K/well and cultured for 1, 4, or 7 days in a humid incubator at 37° C. and at 5% $CO_2$. Calcein AM and Ethidium homodimer-1 were used to stain live/dead cells. The cell images were captured under a fluorescent microscope.

Glass-ceramic discs were prepared from cerammed parts. The precursor glass patties were cerammed in an electronic furnace using a cycle of 700° C. for 2 hr for nucleation and then 800° C. for 4 hr for crystal growth. After ceramming, parts (50.8 mm×50.8 m×1.0 mm thick) were cut from the patties using a diamond saw, and then ground and polished to a 1.0 micron finish using $CeO_2$ slurry. All finished parts were cleaned by sonicating in an ultrasonic sonicater for 10 min.

Ion exchange was accomplished by immersing the finished parts in a $NaNO_3$, in a $KNO_3$, or a bath containing a mixture both salts. The bath was first heated up to 470° C. to obtain a molten salt and then parts were immersed for a suitable time for adequate ion exchange. The ion-exchanged parts were rinsed thoroughly with water and air dry prior to mechanical testing. Flexural strength was tested according to ASTM C1499-15. A ring on ring test-jig equipped with an Instron testing machine with a ring support of 25.4 mm in diameter and a loading ring of 12.7 mm in diameter was performed on finished samples. Flexural strength was determined based on the abovementioned ASTM procedure.

Figure 2:
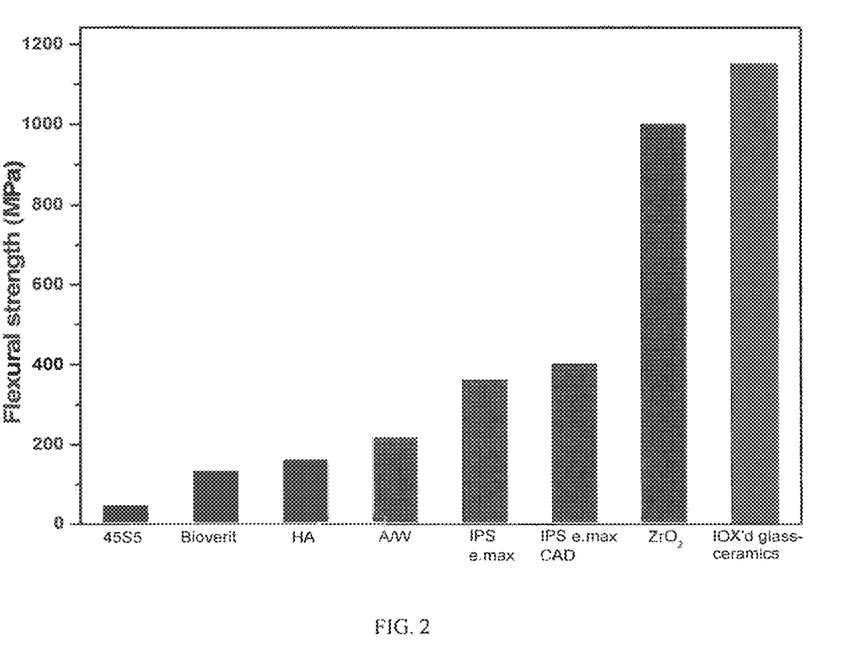
FIG. 2 shows a comparison of flexural strength of selected comparative materials (e.g., 200 to 260 as defined herein) used for biomedical applications including an ion-exchanged glass-ceramic of the presently disclosed composition (270).
Figure 3A:
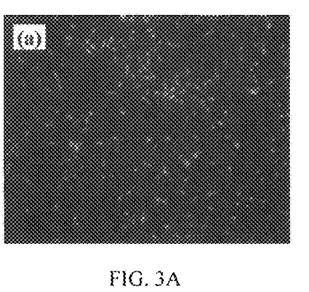
FIGS. 3A to 3I show a cell culture study on glass-ceramics before (3A to 3C) and after ion-exchanging ("IOX") (3D to 3F).
Figure 3B:
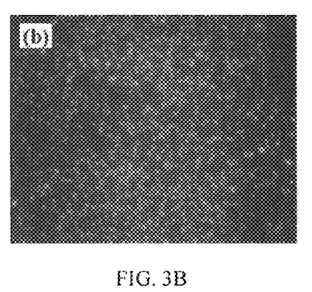
Figure 3C:
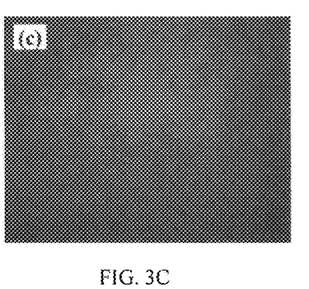
Figure 3D:
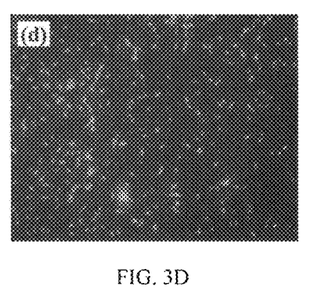
Figure 3E:
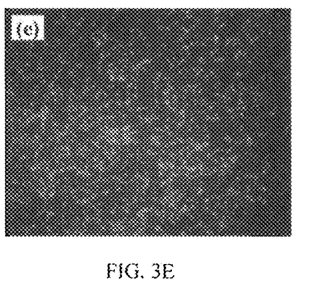
Figure 3F:
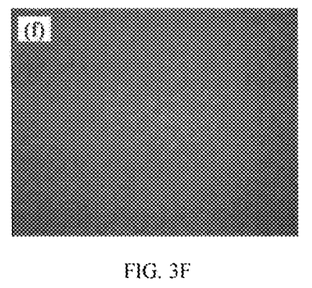
Figure 3G:
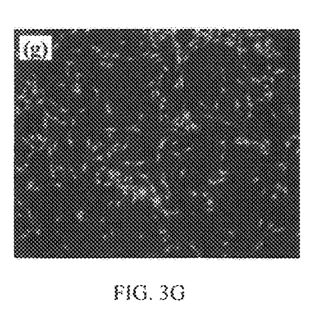
Figure 3H:
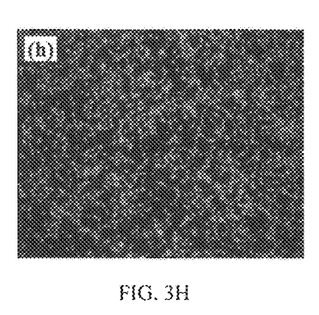
Figure 3I:
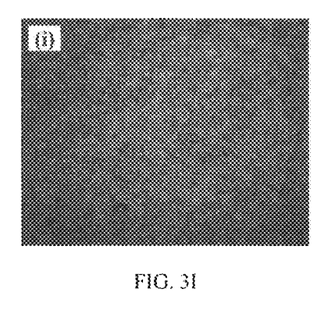

FIG. 2 was a listing of flexural strength from different compositions (200 to 260) from literature and compared to the flexural strength of the disclosed ion exchanged composition (270). The test procedure for example compositions was detailed in the example for FIG. 1.

The disclosure has been described with reference to various specific embodiments and techniques. However, many variations and modifications are possible while remaining within the scope of the disclosure.

What is claimed is:
1. A glass-ceramic composition, comprising:
a first crystalline phase and a second crystalline phase, in combination, comprise a source of:
50 to 75 wt % $SiO_2$,
1 to 5 wt % $Al_2O_3$,
0.1 to 10% $B_2O_3$,
5 to 20 wt % $Li_2O$,
0.5 to 5 wt % $Na_2O$,
0 to 4% $K_2O$,
0.5 to 6 wt % $P_2O_5$
0.5 to 8% $ZrO_2$, and
0.1 to 1.0 wt % $F^-$, based on a 100 wt % total of the composition.
2. The glass-ceramic composition of claim 1 further comprising having composition particles having ion-exchanged surfaces having a reduced lithium ion ($Li^+$) concentration and having at least one of an elevated sodium ion ($Na^+$) surface concentration, an elevated potassium ion ($K^+$) surface concentration, or elevated concentrations of lithium ion ($Li^+$) and sodium ion ($Na^+$) on the surface.
3. The glass-ceramic composition of claim 1 wherein the source is:
50 to 70 wt % $SiO_2$,
1 to 4 wt % $Al_2O_3$,
0.1 to 4% $B_2O_3$,
6 to 18 wt % $Li_2O$,
1 to 4 wt % $Na_2O$,
0 to 3% $K_2O$,
1 to 5 wt % $P_2O_5$
1 to 6% $ZrO_2$, and
0.1 to 1.0 wt % $F^-$, based on a 100 wt % total of the composition.
4. The glass-ceramic composition of claim 3 further comprising having composition particles having ion-exchanged surfaces having a reduced lithium ion ($Li^+$) concentration and having at least one of an elevated sodium

($Na^+$) concentration, an elevated potassium ($K^+$) concentration, or an elevated concentrations of lithium ion ($Li^+$) and sodium ion ($Na^+$).

5. The glass-ceramic composition of claim 1 wherein the first crystalline phase comprises of from 50 to 99 wt % and the second crystalline phase comprises of from 1 to 50 wt % based on a 100 wt % total of the composition.

6. The glass-ceramic composition of claim 1 wherein the first crystalline phase is lithium disilicate, and the second crystalline phase is at least one of wollastonite, fluroapatite, cristobalite, β-quartz, lithiophosphate, or mixtures thereof.

7. A glass-ceramic article comprising:
50 to 75 wt % $SiO_2$,
1 to 5 wt % $Al_2O_3$,
0.1 to 10% $B_2O_3$,
5 to 20 wt % $Li_2O$,
0.5 to 5 wt % $Na_2O$,
0 to 4% $K_2O$,
0.5 to 6 wt % $P_2O_5$,
0.5 to 8% $ZrO_2$, and
0.1 to 1.0 wt % $F^-$, based on a 100 wt % total of the composition.

8. The glass-ceramic article of claim 7 wherein the flexural strength of the article is from 300 to 2,000 MPa.

9. The glass-ceramic article of claim 7 being translucent white or semi-transparent white in color.

* * * * *

UNITED STATES PATENT AND TRADEMARK OFFICE
CERTIFICATE OF CORRECTION

PATENT NO. : 11,446,410 B2
APPLICATION NO. : 17/076410
DATED : September 20, 2022
INVENTOR(S) : Deng et al.

Page 1 of 3

It is certified that error appears in the above-identified patent and that said Letters Patent is hereby corrected as shown below:

On the Title Page

On the page 3, in Column 2, under item (56) "Other Publications", Line 1, delete "Da Vari," and insert -- Davari, --.

On the page 3, in Column 2, under item (56) "Other Publications", Line 2, delete ")." and insert -- . --.

On the page 3, in Column 2, under item (56) "Other Publications", Line 28, delete "MeECH" and insert -- Mech. --.

On the page 3, in Column 2, under item (56) "Other Publications", Line 37, delete "P205" and insert -- $P_2O_5$ --.

On the page 3, in Column 2, under item (56) "Other Publications", Line 38, delete "B203" and insert -- $B_2O_3$ --.

On the page 3, in Column 2, under item (56) "Other Publications", Line 38, delete "Al203" and insert -- $Al_2O_3$ --.

On the page 3, in Column 2, under item (56) "Other Publications", Line 40, delete "Na20-K20-" and insert -- $Na_2O-K_2O-$ --.

On the page 3, in Column 2, under item (56) "Other Publications", Line 41, delete "B203-P205" and insert -- $B_2O_3-P_2O_5$ --.

On the page 3, in Column 2, under item (56) "Other Publications", Line 43, delete "Additiona" and insert -- Addition --.

On the page 3, in Column 2, under item (56) "Other Publications", Line 45, delete "Internaitonal;"

Signed and Sealed this
Twenty-fifth Day of April, 2023

Katherine Kelly Vidal
*Director of the United States Patent and Trademark Office*

CERTIFICATE OF CORRECTION (continued)
U.S. Pat. No. 11,446,410 B2 and insert -- International; --.

On the page 3, in Column 2, under item (56) "Other Publications", Line 48, delete "Na20" and insert -- $Na_2O$ --.

On the page 3, in Column 2, under item (56) "Other Publications", Line 48, delete "B203" and insert -- $B_2O_3$ --.

On the page 3, in Column 2, under item (56) "Other Publications", Line 57, delete "aspromising" and insert -- as promising --.

On the page 3, in Column 2, under item (56) "Other Publications", Line 60, delete "A12O3" and insert -- $Al_2O_3$ --.

On the page 4, in Column 1, under item (56) "Other Publications", Lines 17-18, delete "Si02-Na20-Fe203-Ca0-P205-B203" and insert -- $SiO_2$-$Na_2O$-$Fe_2O_3$-$CaO$-$P_2O_5$-$B_2O_3$ --.

On the page 4, in Column 1, under item (56) "Other Publications", Line 42, delete "B203-Si02-P205-Na20" and insert -- $B_2O_3$-$SiO_2$-$P_2O_5$-$Na_2O$ --.

On the page 4, in Column 1, under item (56) "Other Publications", Lines 46-47, delete "Si02.Na20.CaO.K 20.Mg O.P205" and insert -- $SiO_2$.$Na_2O$.$CaO$.$K_2O$.$MgO$.$P_2O_5$ --.

On the page 4, in Column 1, under item (56) "Other Publications", Line 47, delete "Al203 and B203" and insert -- $Al_2O_3$ and $B_2O_3$ --.

On the page 4, in Column 1, under item (56) "Other Publications", Line 50, delete "inomercementa" and insert -- ionomer cements --.

On the page 4, in Column 2, under item (56) "Other Publications", Line 8, delete "Microplasitcs" and insert -- Microplastics --.

On the page 4, in Column 2, under item (56) "Other Publications", Line 9, delete ")) ." and insert -- ). --.

On the page 4, in Column 2, under item (56) "Other Publications", Line 30, delete "Prepareation" and insert -- Preparation --.

On the page 4, in Column 2, under item (56) "Other Publications", Line 35, delete "stronium" and insert -- strontium --.

On the page 4, in Column 2, under item (56) "Other Publications", Line 38, delete "Manetization" and insert -- Magnetization --.

On the page 4, in Column 2, under item (56) "Other Publications", Line 53, delete "EmpressT2" and insert -- Empress 2 --.

CERTIFICATE OF CORRECTION (continued)
U.S. Pat. No. 11,446,410 B2

On the page 4, in Column 2, under item (56) "Other Publications", Line 53, delete "Empresst" and insert -- Empress --.

On the page 5, in Column 1, under item (56) "Other Publications", Line 22, delete "Monoflurophosphate" and insert -- Monofluorophosphate --.

On the page 5, in Column 1, under item (56) "Other Publications", Line 33, delete "Propmotes" and insert -- Promotes --.

In the Claims

In Column 10, Line 41, in Claim 1, delete "$P_2O_5$" and insert -- $P_2O_5$, --.

In Column 10, Line 60, in Claim 3, delete "$P_2O_5$" and insert -- $P_2O_5$, --.